United States Patent
Sakaguchi et al.

(10) Patent No.: US 7,922,704 B2
(45) Date of Patent: Apr. 12, 2011

(54) NURSING PAD

(75) Inventors: Satoru Sakaguchi, Tokyo (JP); Ayami Suga, Tokyo (JP)

(73) Assignee: Unicharm Corporation, Ehime (JP)

( * ) Notice: Subject to any disclaimer, the term of this patent is extended or adjusted under 35 U.S.C. 154(b) by 87 days.

(21) Appl. No.: 12/173,625

(22) Filed: Jul. 15, 2008

(65) Prior Publication Data

US 2008/0281288 A1   Nov. 13, 2008

Related U.S. Application Data

(63) Continuation of application No. 11/466,780, filed on Aug. 24, 2006, now Pat. No. 7,416,544.

(30) Foreign Application Priority Data

Oct. 11, 2005   (JP) .................................. 2005-296929

(51) Int. Cl.
*A61F 13/15* (2006.01)
*A61F 13/20* (2006.01)

(52) U.S. Cl. ................. 604/385.07; 604/385.01; 450/37

(58) Field of Classification Search .............. 604/385.01, 604/385.07; 450/37, 57–58; 128/889–890, 128/894

See application file for complete search history.

(56) References Cited

U.S. PATENT DOCUMENTS

| | | | | |
|---|---|---|---|---|
| 3,442,268 | A | * | 5/1969 | William ......................... 604/380 |
| 5,683,286 | A | * | 11/1997 | Kielland ......................... 450/37 |
| 5,931,717 | A | | 8/1999 | Lidji |
| 6,241,715 | B1 | | 6/2001 | Houser et al. |

FOREIGN PATENT DOCUMENTS

| JP | 282844 | 4/1953 |
|---|---|---|
| JP | 5767742 | 4/1982 |
| JP | 59-150436 | 10/1984 |
| JP | 7-5619 | 1/1995 |
| JP | 07-5619 | 1/1995 |
| JP | 7-21711 | 4/1995 |
| JP | 7-21712 | 4/1995 |
| JP | 7-21713 | 4/1995 |
| JP | 08-060409 | 3/1996 |

(Continued)

OTHER PUBLICATIONS

International Search Report of PCT/JP2006/316293 issued on Nov. 7, 2006.

(Continued)

*Primary Examiner* — Michele Kidwell

(74) *Attorney, Agent, or Firm* — Lowe, Hauptman, Ham & Berner, LLP

(57) ABSTRACT

The present invention provides a disposable nursing pad having a layered structure of a liquid-permeable sheet, an absorbent body, and a liquid-impermeable sheet. The liquid-permeable sheet and the liquid-impermeable sheet are adhered to each other. This prevents the liquid-permeable sheet from becoming detached from the absorbent body, and provides a nursing pad having an improved capacity to maintain its three-dimensional shape. A pair of pad pieces 2 and 3, each of which has a layered structure of a liquid permeable sheet piece, an absorber, and a liquid-impermeable sheet piece, is joined so as to form a nursing pad 1 having an approximately conical shape. With the nursing pad 1, a connection portion 4 where pad pieces are joined forms a ridge which serves as the center line of the nursing pad 1. The nursing pad 1 can be folded along the ridge.

7 Claims, 6 Drawing Sheets

FOREIGN PATENT DOCUMENTS

| | | |
|---|---|---|
| JP | 08-196603 | 8/1996 |
| JP | 09-137307 | 5/1997 |
| JP | 11-229206 | 8/1999 |
| JP | 2000-226702 | 8/2000 |
| JP | 2004-332178 | 11/2004 |
| JP | 2009030179 | 2/2009 |

OTHER PUBLICATIONS

Notice of Reasons for Rejection issued to Japanese Application No. 2008-148349 mailed Apr. 27, 2010.

* cited by examiner

NURSING PAD

RELATED APPLICATIONS

The present application is a continuation of U.S. application Ser. No. 11/466,780 filed Aug. 24, 2006 now U.S. Pat. No. 7,416,544, which claims priority from, Japanese Application No. 2005-296929, filed Oct. 11, 2005. The disclosures of the above-listed applications are hereby incorporated by reference herein in their entirety.

BACKGROUND OF THE INVENTION

1. Field of the Invention

The present invention relates to a disposable nursing pad for a lactating woman, which has a function of absorbing mother's milk (excess mother's milk) secreted from the breasts (nipples).

2. Related Art

In general, a great amount of a mother's milk is secreted in response to the sucking stimulation from a baby. However, in some cases, the mother's milk leaks without any sucking stimulation. Also, the left and right breasts both respond together. Accordingly, when a mother's breast feeds a baby, the mother's milk is also secreted from the other breast. In order to keep a wearer's clothing dry from such undesired leakage of the mother's milk, a lactating mother wears nursing pads in contact with the inner face of the wearer's underclothing such as a bra or the like, which envelopes the breasts, thereby absorbing the excess mother's milk. In general, such a nursing pad has a layered structure with a surface member which is directly in contact with the breast, an absorbent member for absorbing the mother's milk, and a water-proof member for preventing the absorbed mother's milk from leaking out to the wearer's clothing. Also, a nursing pad with a three-dimensional shape, which is formed beforehand into a shape having a protruding portion at the center thereof such that it can envelope a breast, has been proposed as shown in FIG. 11. This allows the nursing pad to be easier to wear, and improves the degree of fit of the nursing pad with respect to the breast when it is being worn.

Here, the nursing pad is manufactured by press working as follows. First, two-dimensional sheets, which are component layers, are layered so as to form a pad. Then, heat is applied to the entire pad thus formed. However, in some cases, with the nursing pad thus molded into the three-dimensional shape of a dome by the manufacturing process, the nursing pad has a poor capacity to maintain its shape. This leads to a problem in which the nursing pad becomes deformed due to being dampened by mother's milk, or due to the pressure applied thereto from the movement of the wearer. This results in the deterioration of the degree of fit of the nursing pad with respect to the breast of the wearer. Also, there is a problem in that such a nursing pad feels coarse and stiff due to hardening of the component sheets after a heating step, where heat is applied to the nursing pad such that it is formed into the shape of a dome. In order to solve this problem, the aforementioned conventional nursing pad includes a support member which has a lower melting point than that of the water-proof member, and which is provided between the water-proof member and the absorbent member. With such an arrangement, the nursing pad is formed into the shape of a dome by the application of heat at a temperature which is lower than the temperature that causes thermal deformation of the water-proof member, and which is higher than the melting point of the support member. This allows the shape of the support member to be changed, thereby enabling the nursing pad to be formed in the shape of a dome.

Patent Document 1

Japanese Unexamined Patent Application Publication No. 2000-226702

Press working the entire area of the nursing pad allows the absorbent member and the water-proof member to be molded into a three-dimensional shape. However, it is difficult to mold the surface member into the three-dimensional shape. Specifically, the molding of the surface member into the three-dimensional shape leads to it feeling coarse and stiff. The surface member is a component layer which is to be in contact with the skin. Accordingly, a surface member which feels coarse and stiff, leads to friction with the skin, often resulting in causing skin problems. Regarding this point, with the aforementioned conventional arrangement, the component member which is subjected to heat shaping processing is the support member provided between the water-proof member and the absorbent member. While such an arrangement also facilitates the molding of the absorbent member and the water-proof member into a three-dimensional shape, it is difficult to mold the surface member into a three-dimensional shape, since it is not directly in contact with the support member, which is the remaining problem.

In order to prevent the surface member from becoming stiff and coarse, in some cases, a method is employed in which the nursing pad is molded into a three-dimensional shape without the application of heat to the center of the surface member, which is in contact with the nipple. In this case, the center of the surface member is not molded into the three-dimensional shape. This often causes a gap between the absorbent member which has been molded into the three-dimensional shape, and the surface member. Such a gap leads to a problem in which the mother's milk flows through the surface of the surface member on the side in contact with the skin of the wearer or flows through the inside of the surface member. This results in a problem in which the mother's milk does not reach the absorbent member, or a problem in which the surface member comes in contact with the skin of the wearer. On the other hand, let us consider an arrangement in which the surface member and the absorbent member are adhered to each other by adhesive. However, during use of the nursing pad, the absorbent member absorbs the mother's milk. This causes the adhesion of the interface between the absorbent member and the adhesive to deteriorate. This causes the abovementioned gap to occur more often, leading to a reduction of absorption efficiency. This also causes leakage of the mother's milk.

SUMMARY OF THE INVENTION

In order to solve the aforementioned problems, the present invention provides a nursing pad having a structure in which a liquid-permeable sheet which is a surface member, and a liquid-impermeable sheet which is a water-proof member form a single unit, thereby preventing the liquid-permeable sheet and the liquid-impermeable sheet from becoming detached from one another even when damp, while satisfactorily maintaining the nursing pad in a dome-like shape. More specifically, the present invention provides a nursing pad having a structure in which the liquid-permeable sheet and the liquid-impermeable sheet are adhered to each other so as to form a single unit, and the adhesive portion forms a ridge on the center line that passes through the center of the nursing pad. This enables the wearer to wear a nursing pad while maintaining a space between the wearer's nipple and the corresponding portion of the nursing pad.

More specifically, the present invention provides the following arrangements.

The first aspect of the present invention is a nursing pad, which is formed with an approximately conical shape, comprising: a liquid-permeable sheet having a face which is to be in contact with the skin; a liquid-impermeable sheet having a face which is to be in contact with the wearer's clothing; an absorbent body provided between the liquid-permeable sheet and the liquid-impermeable sheet; and an adhesive portion formed at a portion corresponding to the wearer's nipple when the nursing pad is being worn, by directly or indirectly coupling the liquid-permeable sheet and the liquid-impermeable sheet.

According to an aspect of the present invention, the nursing pad has a portion which is a region where a liquid-permeable sheet and a liquid-impermeable sheet are adhered to each other. The adhesive portion corresponds to the position of the wearer's nipple when the nursing pad is being worn. Such a structure provides a space between the wearer's nipple and the nursing pad when the nursing pad is being worn. Furthermore, the liquid-permeable sheet and the liquid-impermeable sheet are formed as a single unit. This prevents the liquid-permeable sheet from becoming detached and moving from its proper position of the nursing pad, even in cases in which the nursing pad is being dampened by mother's milk. This markedly suppresses the frequency of the wearer's nipple directly coming in contact with the liquid-permeable sheet, which markedly prevents the occurrence of friction between the wearer's nipple and the liquid-permeable sheet, thereby suppressing sensations of discomfort or pain due to undesirable pressure and stimulation.

According to an aspect of the present invention, the nursing pad is formed to have an approximately conical shape when the nursing pad is being worn. Here, it is not essential for all the components, which form the nursing pad, to be formed into a more or less circular shape. Each component may be formed into any shape as long as these components form a layered structure in an approximately a conical shape (including a heart-like shape). Also, the nursing pad may be formed into the shape of an acute-angle cone, or into the shape of a gently-sloping cone such as a dome-like shape, depending upon the angle of the apex of the cone (depth of the cup). That is to say, the angle of the apex of the cone (depth of the cup) is not restricted in particular, as long as the nursing pad is formed in a shape that fits the wearer's breast. Note that examples of the methods for molding a series of the liquid-permeable sheet and the liquid-impermeable sheet into a conical shape include a method for forming gathered portions at portions opposite to one another by nipping these portions.

The liquid-permeable sheet and the liquid-impermeable sheet may be indirectly adhered to each other through a region where the absorbent body is provided between these sheets. Alternatively, the liquid-permeable sheet and the liquid-impermeable sheet may be directly adhered to each other without involving a region where the absorbent body is provided between these sheets, as described later.

In a second aspect of the nursing pad described in the first aspect of the present invention, with the adhesive portion being formed in a ridge line extending from one edge of the nursing pad to the other edge through the center thereof.

According to an aspect of the present invention, the adhesive portion is formed along the center line of the nursing pad having an approximately conical shape, and serves as a ridge when the nursing pad is being worn. Accordingly, the apex of the nursing pad having an approximately conical shape is positioned on the adhesive portion. With such an arrangement, the wearer can wear the nursing pad with the apex thereof in a position corresponding to the wearer's nipple, whereupon the nursing pad is fitted to the wearer's breast.

In a third aspect of the nursing pad described in the first or second aspect of the present invention, with the nursing pad has a region where the absorbent body is not provided, corresponding at least to the position where the wearer's nipple is situated when the nursing pad is being worn.

According to an aspect of the present invention, the nursing pad has a region where the absorbent body is provided and a region where the absorbent body is not provided. Accordingly, the adhesive portion has a recess formed from the inner face toward the outer face, as viewed from the side of the wearer's body. The wearer can wear the nursing pad with this portion matching the wearer's nipple, thereby providing a space between the nursing pad and the wearer's nipple in a reliable manner. Furthermore, the space between the wearer's nipple and the liquid-permeable sheet created when the nursing pad is being worn can be adjusted by adjusting the thickness of the absorbent body. In particular, the nipples of lactating women become more protruded than usual. Thus, such an arrangement effectively prevents the wearer's nipple from coming in contact with the liquid-permeable.

In a fourth aspect of the nursing pad described in the first through third aspect of the present invention, the absorbent body is formed of a pair of absorbers, and the adhesive portion is provided between the pair of absorbers.

According to an aspect of the present invention, the absorbent body is formed of a pair of absorbers. This enables the space between the nursing pad and the wearer's nipple to be adjusted not only by adjusting the thickness of the absorbers, but also by adjusting the interval between the absorbers. This enables the nursing pad to be adjusted according to the individual wearer's nipples.

In a fifth aspect of the nursing pad described in the second through fourth aspect of the present invention, the ridge line serves as the axis of a fold along which the nursing pad can be double-folded so as to enclose the liquid-permeable sheet.

According to an aspect of the present invention, the nursing pad is not molded into the three-dimensional shape by the manufacturing process. The wearer forms the folded nursing pad before use, whereupon the nursing pad is formed into a three-dimensional shape. This allows the wearer to carry the nursing pad in a double-folded state and in a compact manner without being concerned about the cup collapsing. Furthermore, such an arrangement provides a cup with a sufficient depth when the nursing pad is being worn. Also, the center line is properly formed, thereby improving the capacity of the cup to maintain its shape as formed when the nursing pad is being worn. This effectively prevents deformation of the nursing pad when it is being worn.

In a sixth aspect of the nursing pad described in the fifth aspect of the present invention, the nursing pad further includes: a pad piece having a liquid-permeable sheet piece and a liquid-impermeable sheet piece, a connection portion in which a pair of pad pieces are joined, and serves as said folding axis. The absorber is sandwiched between the liquid-permeable sheet piece and liquid-impermeable sheet piece.

According to an aspect of the present invention, the nursing pad, which is to be put on wearer's a breast, has a structure in which two pad pieces are joined by connecting a part of the perimeter of one pad piece and a part of the perimeter of the other pad piece, such that the nursing pad has an approximately conical shape when the nursing pad is being worn. On the other hand, conventional nursing pads are molded into a three-dimensional shape during the molding process. However, such a conventional nursing pad having a deep cup is subject to creases, leading to a problem of sensations of discomfort when being worn. In order to solve the aforementioned problem, in general, such conventional nursing pads have been formed with a shallow cup, so as not to create creases. However, the breasts of lactating women become more protruded than usual. Accordingly, such a conventional nursing pad with a shallow cup has difficulty in being properly fit to the breast. On the other hand, the nursing pad according to the present invention provides a cup with a sufficient depth, without creases from adjusting the size of the pad pieces as appropriate. Furthermore, the nursing pad according to the present invention is formed using an adhesion step in which the pad pieces are adhered to each other at adhesive portions, each of which has a certain width, and which have been provided to the pad pieces, instead of having a press working step in which the entire area of the nursing pad is press worked. This improves the capacity of the cup to maintain its shape. Note that the adhesive portions where a pair of pad pieces is adhered are preferably provided with lengths between 30% and 50% of the overall perimeter of the pad pieces.

The aforementioned the pair of pad pieces is preferably formed to be completely symmetrical with each other, with the aforementioned adhesive portion where the pad pieces are joined as the axis of a fold, thereby allowing the nursing pad to be folded with these pad pieces matching one another. Also, the pair of pad pieces may be formed in an asymmetrical manner such that they can be adjusted to diverse individual breast shapes. Examples of the asymmetrical shapes employed for the pair of pad pieces include: an arrangement in which one pad piece of the pair of pad pieces is formed with a larger size than that of the other pad piece; and an arrangement in which a notch is formed in one pad piece. Such an arrangement prevents the nursing pad from protruding from the wearer's underclothing, such as a bra or the like.

In a seventh aspect of the nursing pad described in the fifth or sixth aspect of the present invention, the folding axis is formed of a curve with a continuous curvature, or formed of two lines connected to each other at a certain position.

According to an aspect of the present invention, the axis of a fold, along which the nursing pad is to be folded, forms a ridge line. Accordingly, the axis of a fold is formed in a shape protruding toward the wearer's clothing when the nursing pad is being worn. This allows the nursing pad to be easily fitted to the wearer's breast when the nursing pad is being worn. Note that the axis of a fold is preferably formed with a curvature that is gradually reduced in a direction towards the upper side of the wearer's breast when the nursing pad is being worn. With this arrangement, the nursing pad matches the profile of the wearer's breast.

In a eighth aspect of the nursing pad described in the fifth through seventh aspect of the present invention, the nursing pad further includes a apex portion being positioned below the center thereof along the vertical direction when the nursing pad is being worn.

According to an aspect of the present invention, the nursing pad is configured such that the highest portion of the cup thereof is positioned somewhat below the center of the wearer's breast when the nursing pad is being worn. The reason is as follows. That is to say, in general, the nipples of women are not positioned at the center of the breasts, but are positioned somewhat below the center. In addition, many mothers breast feed a baby with one breast while the baby is held below the breasts. Accordingly, in many cases, the breasts have the kind of shape described above. Consequently, the nursing pad according to the present invention is formed into a shape corresponding to this kind of position of the wearer's nipple.

Such a shape of the nursing pad improves the degree of fit of the nursing pad with respect to the breast of the wearer.

In a ninth aspect of the nursing pad described in the sixth through eighth aspect of the present invention, the length of the connection portion where the pair of pad pieces is joined being smaller than the length of the pad piece along the longitudinal direction thereof.

According to an aspect of the present invention, each of the aforementioned pad pieces is formed in a modified egg (or oval) shape. With such an arrangement, a pair of the pad pieces is joined together, with the perimeter of the nursing pad extending from the adhesive portion forming an approximately heart-shaped curved surface with the adhesive portion as the border. Accordingly, the length of the aforementioned adhesive portion is smaller than the length of the aforementioned pad piece along the longitudinal direction. Such a structure allows the wearer to easily decide the axis of a fold, thereby making the nursing pad easier to fold.

ADVANTAGES

As described above, according the present invention, the liquid-permeable sheet and liquid-impermeable sheet are directly or indirectly adhered to each other. This prevents the liquid-permeable sheet from becoming detached from the absorbent body even in cases in which the nursing pads are damp while being worn. Furthermore, such an arrangement suppresses leakage of the mother's milk while preventing the mother's milk from remaining on the wearer's skin. Thus, the present invention provides a nursing pad having a function of keeping the wearer's nipple sanitary. Furthermore, according to the present invention, the nursing pad can be molded into the three-dimensional shape of a dome without creating undesired creases, which causes feelings of discomfort, while the liquid-permeable sheet, which is to be in contact with the wearer's skin, is kept soft. Furthermore, such an arrangement exhibits an improved capacity to maintain its shape. Thus, the present invention provides a nursing pad having a function of alleviating the occurrence of stimulation due to friction between the wearer's nipple and the nursing pad.

DETAILED DESCRIPTION OF THE INVENTION

Detailed description will be made below regarding preferable embodiments according to the present invention with reference to accompanying drawings. Note that, in order to describe preferable specific arrangements according to the present invention, the embodiments described below involve various technical restrictions as appropriate. However, the present invention is not restricted to such arrangements as long as no particular description limits the scope of the present invention.

Basic Structure of a Nursing Pad

Figure 1:
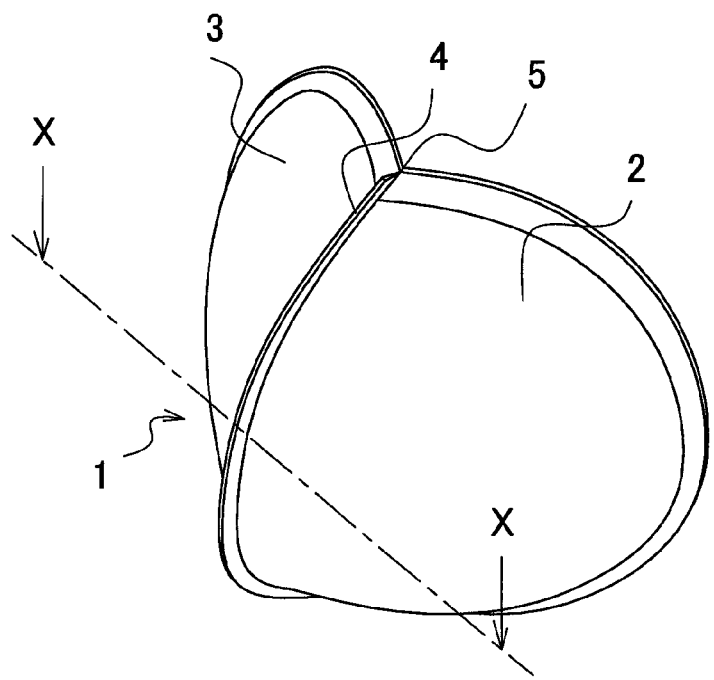
FIG. 1 is an external perspective view which shows a nursing pad according to the present invention.
Figure 2:
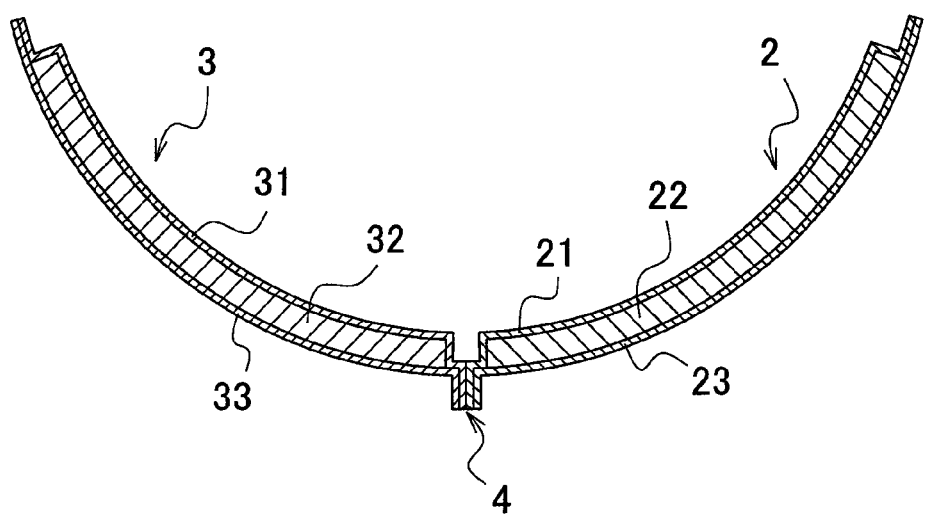
FIG. 2 is a cross-sectional view taken along line X-X in FIG. 1.
Figure 3:
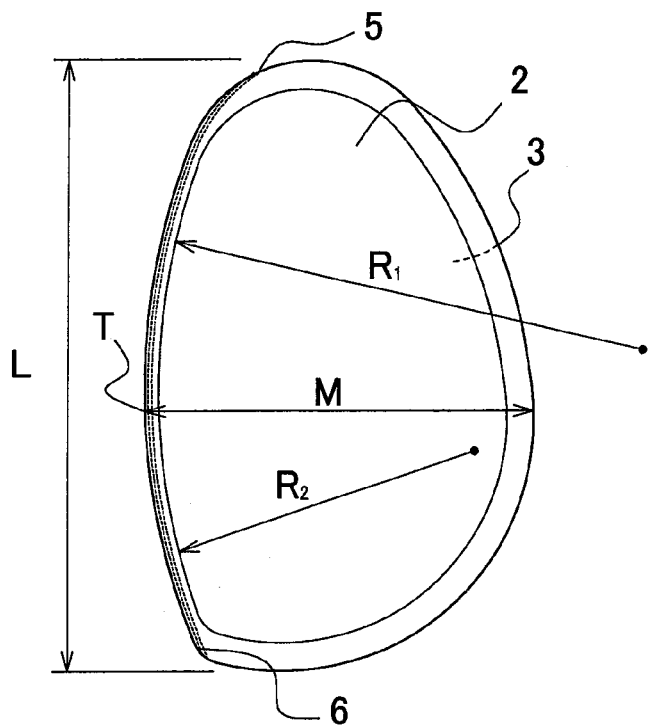
FIG. 3 is a diagram which shows the nursing pad according to the present invention in a folded state.
Figure 4:
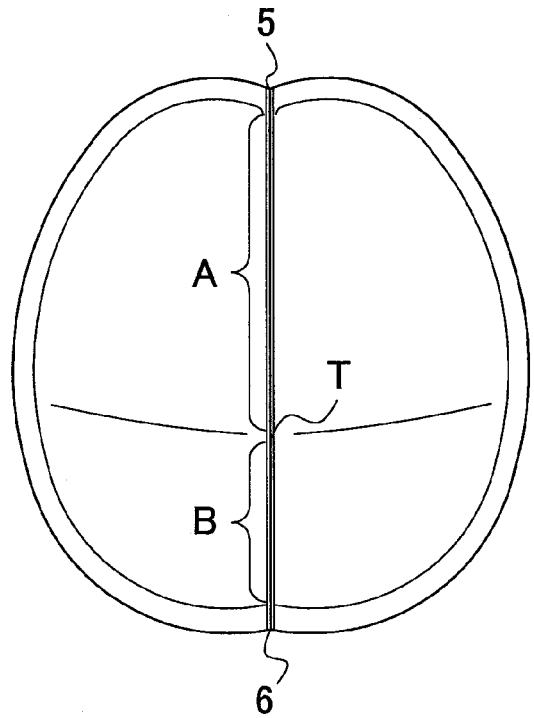
FIG. 4 is a diagram which shows the top view of the nursing pad according to the present invention while the nursing pad is being worn.
Figure 5:
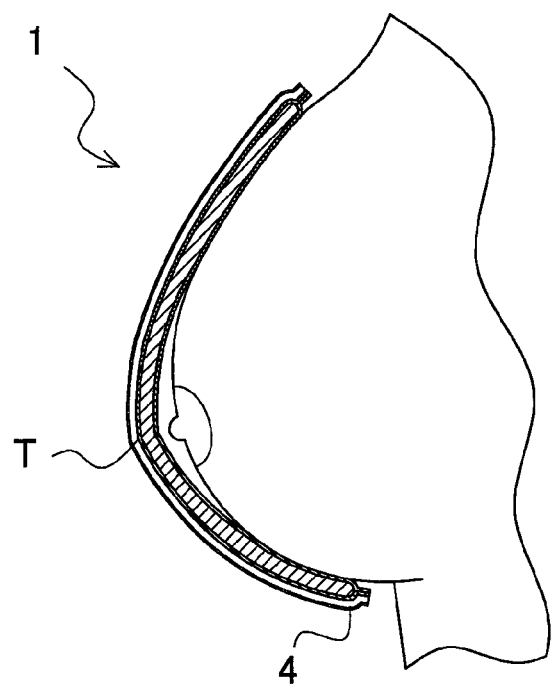
FIG. 5 is a schematic side cross-sectional view which shows the nursing pad according to the present invention in a state in which it is being worn by the wearer.
Figure 6:
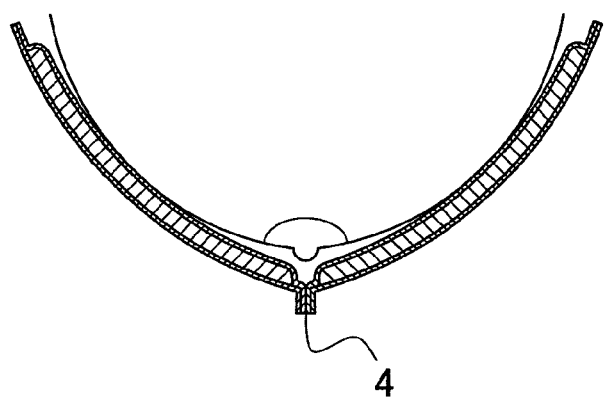
FIG. 6 is a schematic top cross-sectional view which shows the nursing pad according to the present invention in a state in which it is being worn by the wearer.
Figure 7:
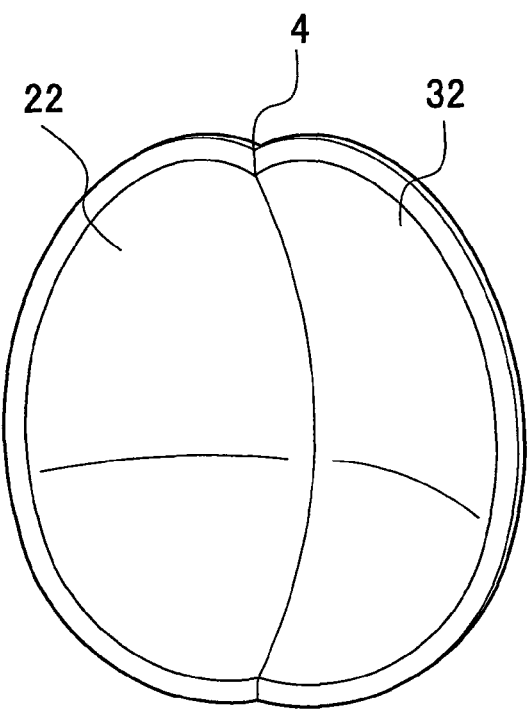
FIG. 7 is a diagram which shows the nursing pad according to the present invention, as viewed from the side where the nursing pad is to be in contact with the wearer's body.
Figure 8:
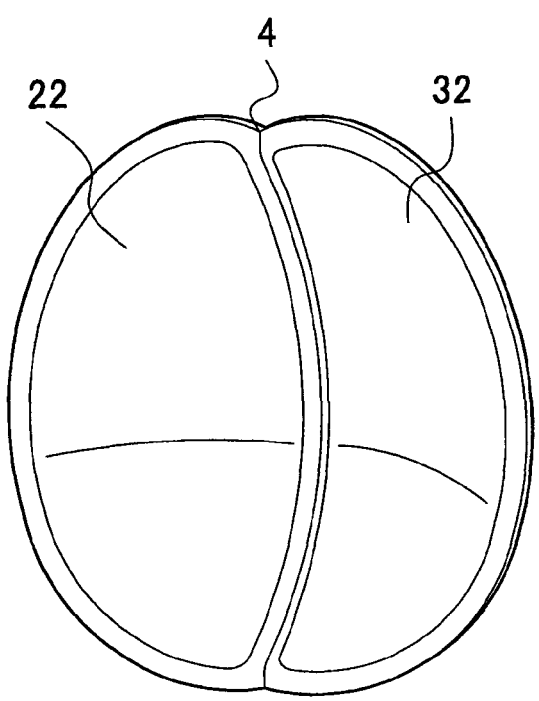
FIG. 8 is a diagram which shows the nursing pad according to the present invention, as viewed from the side where the nursing pad is to be in contact with the wearer's body.

FIG. 1 is an external perspective view which shows a nursing pad according to the present embodiment, as viewed from the side of the surface thereof which is to be in contact with the wearer's clothing. FIG. 2 is a cross-sectional view taken along line X-X in FIG. 1. FIG. 3 is a diagram which shows the nursing pad in a folded state before it is to be used. FIG. 4 is a diagram for showing the top view of the nursing pad when it is being worn. FIGS. 5 and 6 are schematic cross-sectional views, each of which shows an internal structure of the nursing pad in a state in which it is worn by the wearer. FIGS. 7 and 8 are external perspective views, each of which shows the nursing pad, as viewed from the side of the wearer's body.

As shown in FIG. 1, a nursing pad 1 according to the present embodiment is formed such that it has a three-dimensional conical shape when it is being worn, thereby allowing the nursing pad to easily be fitted to the breast. The nursing pad 1 has a structure in which a pad piece 2 and a pad piece 3 are adhered to each other at a connection portion 4 in the form of a film by the application of heating and pressure thereto. Specifically, as shown in FIG. 2, the nursing pad 1 comprises: the pad piece 2 having a layered structure of a liquid-permeable sheet piece 21 which is to be in contact with the skin, an absorber 22 for absorbing mother's milk, and a liquid-impermeable sheet piece 23 which is to be in contact with the wearer's underclothing; and the pad piece 3 having a layered structure of a liquid-permeable sheet piece 31, an absorber 32, and a liquid-impermeable sheet piece 33. The liquid-permeable sheet piece 21 and the liquid-impermeable sheet piece 23 are adhered to each other with the absorber 22 being enclosed therebetween, thereby forming the pad piece 2. The pad piece 3 is formed by adhering the liquid-permeable sheet piece 31 and the liquid-impermeable sheet piece 33 to each other in the same way as with the pad piece 2. Then, the pad piece 2 and the pad piece 3 are joined together by adhering a part of the perimeter, which is an adhesive portion, of the pad 2, to that of the pad 3, thereby forming the connection portion 4 of the nursing pad 1. The connection portion 4 serves as a ridge, which is the center line of the nursing pad 1 when the nursing pad 1 is being worn.

With the nursing pad 1, the aforementioned connection portion 4 prevents the liquid-permeable sheet pieces 21 and 31 from becoming detached from the absorbers 22 and 32, respectively, even in cases in which the liquid-permeable sheet piece 21 or 31 being damp by the leakage of mother's milk from the wearer's nipples when it is being worn. Thus, the nursing pad 1 protects the wearer's nipple while preventing the liquid-permeable sheet pieces 21 and 31 from being in contact with the skin without the absorbers 22 and 32.

The pad pieces 2 and 3 are formed to be completely symmetrical with each other. This allows the nursing pad 1 to be folded, with the liquid-permeable sheet pieces 21 and 31 being brought together with the connection portion 4 as the axis of a fold, such that the surfaces of the liquid-permeable sheet pieces 21 and 31, which are to be in contact with the skin, are in contact with each other. This provides a compact portable nursing pad. In addition, such a portable nursing pad remains folded when it is being carried. This protects the nursing pad 1 from collapsing before use, thereby avoiding a situation in which the nursing pad 1 does not provide a suitable approximately conical shape, and cannot be fit to the breast.

The pad piece 2 is not formed in a completely semi-circular shape, but in a modified egg shape. This is due to the fact that the top portion T, which corresponds to the widest portion, i.e., which serves as the apex of the cup of the nursing pad 1 when it is being worn, is not formed at the center. The top portion T is formed at a position somewhat below the center along the longitudinal direction of the center line which serves as a ridge when the pad pieces 2 and 3 are opened horizontally, as shown in FIG. 4. The reason why such a shape is employed is that the nipples of the lactating woman are positioned below the centers of the breasts, and the nursing pad 1 should be suitably formed for breasts in such a state. Accordingly, the nursing pad 1 has a portion A which is larger than a portion B, with the top portion T as the border between the portions A and B. In such a structure, each of the pad pieces 2 and 3 is formed with a radius of curvature changing from the radius R1 to the smaller radius R2, with the top region T as the border, providing the top region T somewhat below the center of the connection portion 4, which serves as a ridge. Note that, giving consideration to the size of the breasts of the lactating woman, the pad piece 2 is preferably formed with a length L which is equal to or greater than 100 mm and is equal to or smaller than 200 mm, and with a width M is equal to or greater than 50 mm and equal to or smaller than 100 mm; and is more preferably formed with a length L of 125 mm, and with a width M of 75 mm.

As described above, the aforementioned pad pieces are formed in a modified egg shape. With the present embodiment, the pair of pad pieces is joined to each other. In such an arrangement, the perimeters 5 and 6 of the pad pieces 2 and 3 extending from the connection portion 4 form a heart-shaped curved surface with the connection portion as the border therebetween. Accordingly, the length of the connection portion 4 is shorter than the length of the aforementioned pad pieces along the line L in the longitudinal direction. Such a structure allows the wearer to easily decide the axis of a fold, thereby making it easier to fold the nursing pad 1.

When the nursing pad 1 is being worn, there is a gap between the breast and the nursing pad 1 on the inner side of the top portion T, which is the apex of the cup, and the wearer is able to wear the nursing pad 1 without the wearer's nipple being in contact with the nursing pad 1. Accordingly, giving consideration to the state in which the wearer's nipple comes in contact with the nursing pad 1, there is no need to soften the center of the nursing pad 1. This improves the capacity of the cup to maintain its shape. Furthermore, this protects the wearer's breasts from becoming damp, even in cases in which the nursing pad 1 is damp, thereby keeping the wearer's sensitive nipples sanitary.

With the nursing pad 1 in a folded state, the absorbers 22 and 32 are separated from each other. Upon opening the pad pieces 2 and 3 horizontally when the nursing pad 1 is to be worn, the pad pieces 2 and 3 are connected through the connection portion 4, as shown FIG. 7. This enables the mother's milk which leaked from the nipple to be absorbed quickly. On the other hand, the length and size of the breast differs among individuals. In order to solve such a problem, the wearer can wear the nursing pad 1 with the pad pieces 2 and 3 being connected to each other while the absorbers 22 and 32 remain separated from one another, as shown in FIG. 8. This allows the wearer to wear the nursing pad 1 with a larger space between the wearer's nipple and the nursing pad 1.

OTHER EMBODIMENTS

Figure 9:
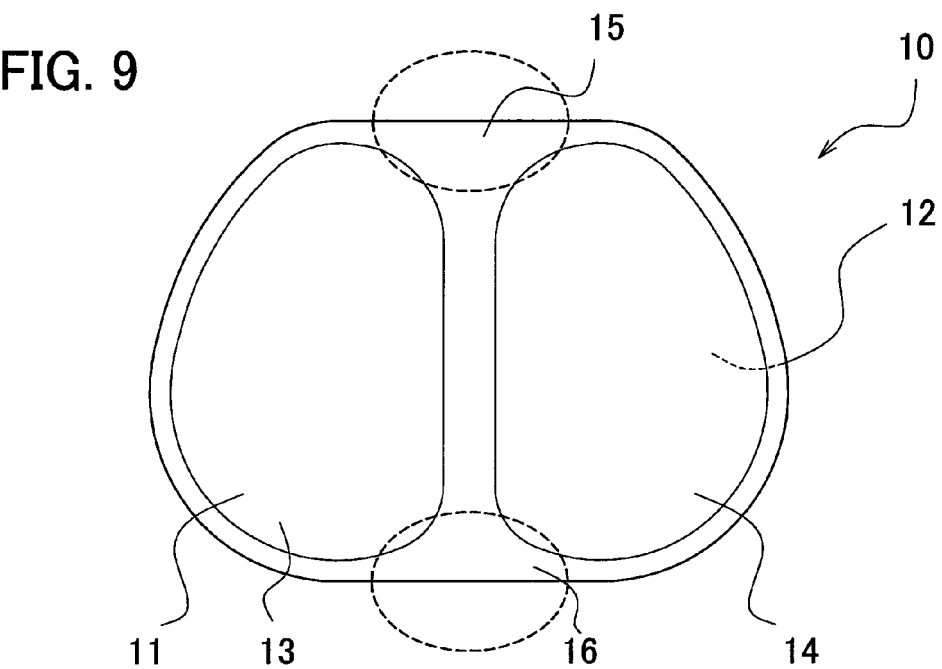
FIG. 9 is a nursing pad according to another embodiment of the present invention.
Figure 10:
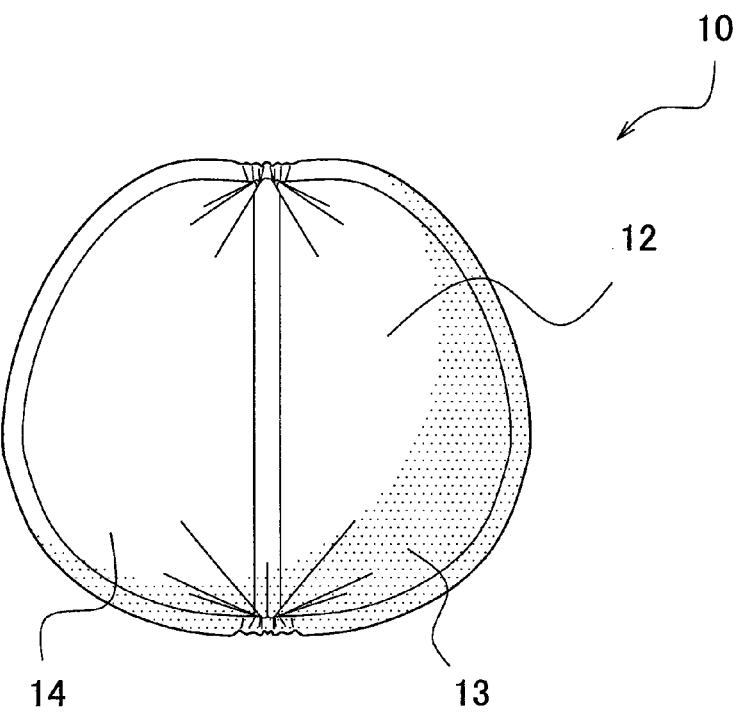
FIG. 10 is the nursing pad according to the embodiment of the present invention.
Figure 11:
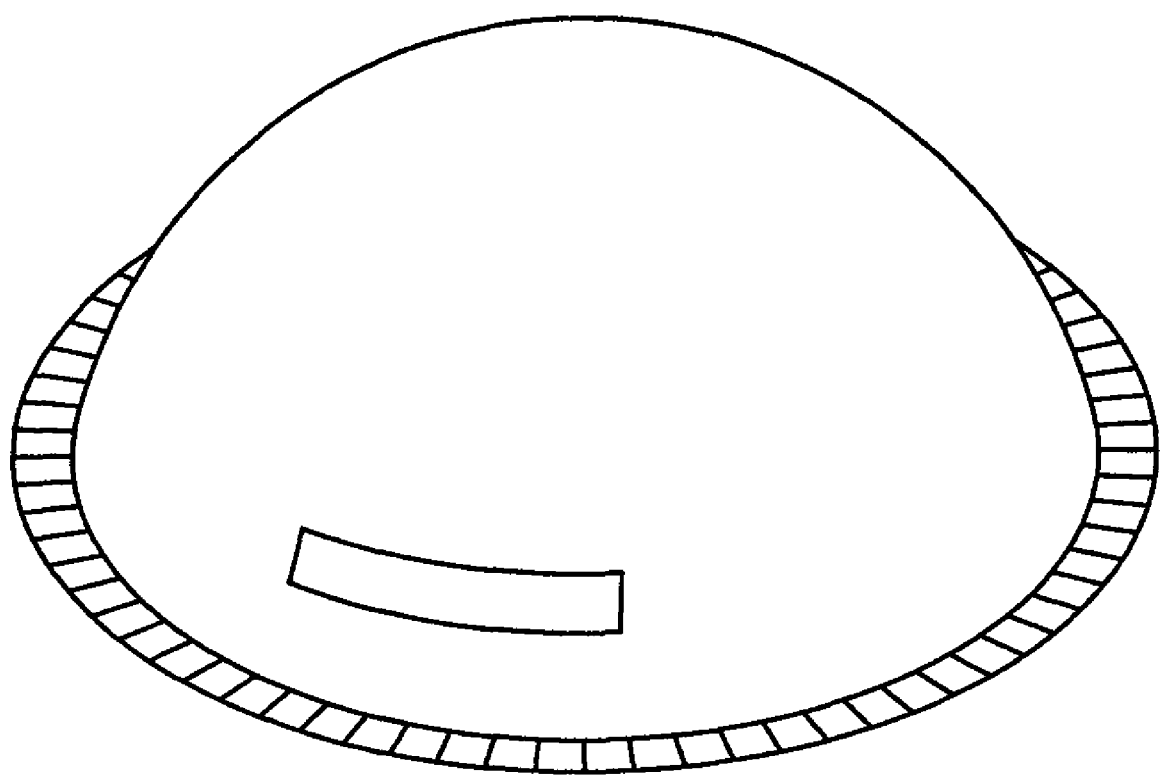
FIG. 11 is a diagram which shows an example of a conventional nursing pad.

FIG. 9 is a developmental view, which shows a nursing pad formed of a series of a liquid-permeable sheet and a liquid-impermeable sheet, as viewed from the side of the face thereof, which is to be in contact with the skin. FIG. 10 is a diagram which shows the nursing pad including gathered portions, as viewed from the side of the outer surface thereof which is to be in contact with the wearer's clothing.

A nursing pad 10 according to the present embodiment has a structure in which absorbers 13 and 14, which are formed to be completely symmetrical with each other, are sandwiched between a series of a liquid-permeable sheet 11 and a liquid-impermeable sheet 12. Furthermore, the regions 15 and 16, which are enclosed by dotted lines in FIG. 9, are gathered, thereby forming the nursing pad 10 into the three-dimensional shape as shown in FIG. 10.

Material of the Nursing Pad

The liquid-permeable sheet can be formed of hydrophilic fibrous non-woven fabric. In addition, the liquid-permeable sheet may be formed of hydrophobic fibrous non-woven fabric having a great number of pores.

Examples of the materials employed for the liquid-impermeable sheet include: an air-permeable and liquid-impermeable drawn plastic film containing inorganic fine particles such as silica, aluminum oxide, or the like; a laminate of liquid-impermeable film and a fibrous non-woven fabric; an air-permeable and a liquid-impermeable film and a fibrous non-woven fabric; etc. Also, the liquid-impermeable sheet may be formed of a composite non-woven fabric having a laminate structure of spunbonded non-woven fabric and a meltblown non-woven fabric.

Examples of the materials employed for the absorber include: a mixture of a particulate or fibrous high water absorption polymer and fluff pulp; a mixture of particulate or fibrous high water absorption polymer, fluff pulp, and thermoplastic synthetic resin fiber. The material is pressed into a sheet with a predetermined thickness, thereby forming the absorber employed in the above embodiments. The absorber thus formed by press processing has a higher rigidity than that of the liquid-permeable sheet and liquid-impermeable sheet formed as described above. Note that, the entire area of the absorber is preferably wrapped in tissue paper in order to prevent the absorber losing its shape, and to prevent loss of the polymer from the absorber.

The absorber is adhered to the inner face of the liquid-permeable sheet or the liquid-impermeable sheet through the tissue paper using a hot melt adhesive or the like. Note that an arrangement may be made employing an SM non-woven fabric or an SMS non-woven fabric, instead of the tissue paper. Here, the SM non-woven fabric and the SMS non-woven fabric are each a composite non-woven fabric formed into the shape of a sheet having a laminate structure, in which a fibrous non-woven fabric which is formed with a high strength and high flexibility using a spun-bonding method, is provided to at least one face of a fibrous non-woven fabric, which is formed with a high fiber density using a meltblown method. In other words, the SM non-woven fabric and the SMS non-woven fabric have a multi-layered structure of spunbonded non-woven fabric and meltblown non-woven fabric. In such an arrangement, employing such a composite non-woven fabric, the fibers which form the fabric exhibit hydrophobicity. Accordingly, the absorber is preferably subjected to hydrophilic processing in order to improve the liquid-permeability.

The adhesive is preferably applied to the sheet or non-woven fabric by any one of a spiral manner, an undulating manner, a zigzag manner, a dotted manner, and a stripe manner. When the adhesive is applied to the sheets or the non-woven fabric in such a manner, these sheets are adhered to each other in a discontinuous manner, thereby connecting the absorber to the sheet in a discontinuous manner. As an adhesive, a hot melt adhesive or the like is employed. Either an olefin adhesive or a styrene rubber adhesive can be employed as such an adhesive.

Examples of arrangements for fitting the nursing pad to the wearer's clothing include: an arrangement in which a styrene rubber adhesive is applied to the liquid-impermeable sheet; an arrangement in which a male mechanical fastener having multiple hooks is provided to the liquid-impermeable sheet.

The fibrous non-woven fabric which can be employed in the present embodiment may be manufactured using any one of a spun-lace method, a needle punch method, a meltblown method, a thermal-bond method, a spun-bonding method, and a chemical-bonding method. The hydrophilic fibrous non-woven fabric can be formed of any one of fiber selected from among a synthetic fiber, semi-synthetic fiber, and a regenerated fiber, which have been subjected to hydrophilic processing, or a composite fiber formed of a mixture of these fibers. The hydrophobic fibrous non-woven fabric may be formed of synthetic fiber. The hydrophobic fibrous non-woven fabric may contain semi-synthetic fiber and regenerated fiber, which have been subjected to water-repelling process. The synthetic fiber which can be employed is not restricted in particular. Specific examples of the synthetic fibers which can be employed include: a polyester fiber; a polyacrylonitrile fiber; a polyvinyl chloride fiber; a polyethylene fiber; a polypropylene fiber; and a polystyrene fiber. Examples of the synthetic composite fibers which can be employed include: a sheath-core type composite fiber; a tandem composite fiber; a non-circular hollow fiber; microporous fiber; jointed composite fiber; etc.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. A nursing pad comprising:
a liquid-permeable sheet adapted to face, in use, a wearer's skin;
a liquid-impermeable sheet adapted to face, in use, away from the wearer's skin;
an absorbent body provided between said liquid-permeable sheet and said liquid-impermeable sheet, and
a separating portion by which first and second portions of the absorbent body are separated from each other in a first direction,
wherein the separating portion extends in a second direction substantially orthogonal to the first direction and defines a folding axis about which the nursing pad is foldable in two, said folding axis being the only preformed folding line of the nursing pad, wherein the liquid-permeable sheet and the liquid-impermeable sheet are directly bonded together at the separating portion, and said nursing pad is free of any through holes along said folding axis; and wherein the separating portion meets a periphery of the nursing pad at two opposite areas, each of said areas comprising a fold in which the liquid-permeable sheet or the liquid-impermeable sheet is folded to face itself, wherein the periphery of the nursing pad is recessed inward along the folding axis at said two opposite areas.

2. The nursing pad according to claim 1, wherein the folding axis is a curve with a continuous curvature.

3. The nursing pad according to claim 1, further comprising an apex portion at a center thereof on the folding axis when the nursing pad is being worn.

4. A nursing pad comprising:
a liquid-permeable sheet adapted to face, in use, a wearer's skin;
a liquid-impermeable sheet adapted to face, in use, away from the wearer's skin;
an absorbent body provided between said liquid-permeable sheet and said liquid-impermeable sheet, and
a separating portion by which first and second portions of the absorbent body are separated from each other in a first direction,
wherein the separating portion extends in a second direction substantially orthogonal to the first direction and defines a folding axis about which the nursing pad is foldable in two,
wherein the liquid-permeable sheet and the liquid-impermeable sheet are directly bonded together at the separating portion, and said nursing pad is free of any through holes along said folding axis; and
wherein the separating portion meets a periphery of the nursing pad at two opposite areas, each of said areas comprising a fold in which the liquid-permeable sheet or the liquid-impermeable sheet is folded to face itself wherein each of said areas includes multiple gathers.

5. The nursing pad according to claim 1, wherein the folding axis is a straight line.

6. The nursing pad according to claim 1, wherein, in the fold, the liquid-permeable sheet or the liquid-impermeable sheet is folded along a fold line oriented in the second direction.

7. A nursing pad comprising:
a liquid-permeable sheet adapted to face, in use, a wearer's skin;
a liquid-impermeable sheet adapted to face, in use, away from the wearer's skin;
an absorbent body provided between said liquid-permeable sheet and said liquid-impermeable sheet, and
a separating portion by which first and second portions of the absorbent body are separated from each other in a first direction,
wherein the separating portion extends in a second direction substantially orthogonal to the first direction and defines a folding axis about which the nursing pad is foldable in two, said folding axis being the only preformed folding line of the nursing pad,
wherein the liquid-permeable sheet and the liquid-impermeable sheet are directly bonded together at the separating portion, and said nursing pad is free of any through holes along said folding axis; and
wherein the separating portion meets a periphery of the nursing pad at two opposite areas, each of said areas comprising a fold in which the liquid-permeable sheet or the liquid-impermeable sheet is folded to face itself,
wherein the periphery of the nursing pad is recessed inward along the folding axis at the fold in which liquid-permeable sheet is folded to face itself.

* * * * *